(12) United States Patent
Tets et al.

(10) Patent No.: US 9,895,371 B2
(45) Date of Patent: Feb. 20, 2018

(54) FUNGICIDAL AGENT

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Viktor Iosifovich Krutikov, St. Petersburg (RU)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 0 days.

(21) Appl. No.: 15/321,601

(22) PCT Filed: Jun. 24, 2014

(86) PCT No.: PCT/RU2014/000452
§ 371 (c)(1),
(2) Date: Dec. 22, 2016

(87) PCT Pub. No.: WO2015/199572
PCT Pub. Date: Dec. 30, 2015

(65) Prior Publication Data
US 2017/0157122 A1   Jun. 8, 2017

(51) Int. Cl.
| C07D 239/545 | (2006.01) |
| A61K 31/513 | (2006.01) |
| A01N 43/54 | (2006.01) |
| C07C 215/10 | (2006.01) |
| A01N 33/08 | (2006.01) |
| A61K 31/133 | (2006.01) |

(52) U.S. Cl.
CPC ............ *A61K 31/513* (2013.01); *A01N 33/08* (2013.01); *A01N 43/54* (2013.01); *A61K 31/133* (2013.01); *C07C 215/10* (2013.01); *C07D 239/545* (2013.01)

(58) Field of Classification Search
CPC .... C07D 239/545; A01N 43/54; A01N 33/08; A61K 31/513
See application file for complete search history.

(56) References Cited

U.S. PATENT DOCUMENTS

| 3,361,745 A | 1/1968 | Schroeder et al. |
| 6,730,787 B1 | 5/2004 | Krutikov et al. |
| 8,987,277 B2 | 3/2015 | Tets et al. |
| 2007/0027034 A1 | 2/2007 | Tank et al. |
| 2010/0179204 A1 | 7/2010 | George et al. |
| 2013/0261301 A1 | 10/2013 | Tets et al. |

FOREIGN PATENT DOCUMENTS

| EP | 2650285 A1 | 10/2013 |
| RU | 2198166 C2 | 2/2003 |
| RU | 2260590 C1 | 9/2005 |
| RU | 2448960 C1 | 4/2012 |
| RU | 2525911 C1 | 8/2014 |
| WO | 2000034250 A1 | 6/2000 |
| WO | 2005103014 A1 | 11/2005 |
| WO | 2008117037 A1 | 10/2008 |

OTHER PUBLICATIONS

International Search Report Issued in PCT/RU2014/000452 dated Mar. 19, 2015; English Translation Thereof; 2 pages.
Berkengeim et al., "Chemistry and Technology of Synthetic Drugs", The Main Edition of the Chemical Literature, Moscow, 1935, p. 42; English Translation Thereof.
European Extended Search Report dated Jun. 11, 2014 which issued during prosecution of European Application No. 11847307.3, 4 pages.
International Search Report and Written Opinion dated Aug. 25, 2011, which issued during prosecution of International Application No. PCT/RU2011/000140, 10 pages; English Translation thereof.
International Preliminary Report on Patentability dated Jan. 18, 2013, which issued during prosecution of International Application No. PCT/RU2011/000140, 11 pages; English Translation thereof.
Krutikov, V. I. et at, "5-Arylideneaminouracils I. Synthesis and the Influence of Physico-Chemical Parameters on the Level of Biological Activity", The journal of general chemistry (2009), vol. 79, Issue 5, pp. 813-818; English Translation Thereof; (Russian Citation: Krutikov, V. I. et al. "5-Arilidenaminouratsily, I. Sintez, vliyanie fiziko-khimicheskikh parametrov na uroven biologicheskoy aktivnosti", Zhumal obschey khimii, 2009, vol. 79(5), pp. 813-888.)

(Continued)

*Primary Examiner* — Deepak Rao
(74) *Attorney, Agent, or Firm* — Troutman Sanders LLP

(57) ABSTRACT

The invention relates to a novel fungicidal agent in the form of a salt associate having the structural formula shown. The agent can be used for treating diseases caused by fungi, and also for preventing fungal damage to various materials and agricultural products. The present fungicidal agent is an associate of 5-[3,5-dichloro-2-hydroxy benzylidene)amino]-4-hydroxy-1H-pyrimidine-2-on with 1,2,3,4,5-pentahydroxy-6-methylaminohexane and has the formula (I).

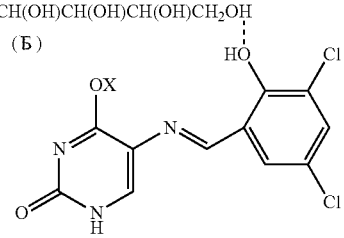

This fungicidal agent exhibits a broad range of activity and high solubility, which increases the effectiveness of the use thereof in the form of solutions. Compounds were obtained in a crystalline form, and the structure thereof was established by means of magnetic resonance spectra in dimethyl sulfoxide.

32 Claims, 1 Drawing Sheet

(56) References Cited

OTHER PUBLICATIONS

Tyukavkina et al., "Bioorganic Chemistry" 4th Edition, Moscow (2005), pp. 304-305; English Translation Thereof; (Russian Citation: Tyukavkina et al. "Bioogranicheskaya khimiya" Moscow <<Drofa>>2005, pp. 304-305.).

Group 1: Alkali Metals. Available from <http://web.archive,org/web/20080410115147/http/www.rsc.org/chemsoc/ visualelements/pages/data/intro_groupi_data.html>, published: Apr. 10, 2008 3 pages.

Krutikov, V. 1. et al., "5-Arylideneaminouracils: II. 1 Synthesis of Sodium and Ammonium Salts", Russian Journal of General Chemistry (2009) vol. 79, No. 5 pp. 991-995.

Written Opinion of The International Searching Autholity dated Mar. 19, 2015, which issued in International Application No. PCT/RU2014/000452, 7 pages; English Translation Thereof.

International Preliminary Report on Patentability dated Dec. 27, 2016, which issued in PCT/RU2014/000452, 6 pages.

European Extended Search Report Issued in European Application No. 14896241.8 dated Dec. 7, 2017, 10 pages.

Yamashita, H. et al., "Coformer Screening Using Thermal Analysis Based on Binary Phase Diagrams", Pharmaceutical Research (2014), vol. 31, No. 8, pp. 1946-1957.

Yadav, A. V. et al., "Co-Crystals: A Novel Approach to Modify Physicochemical Properties of Active Pharmaceutical ingredients", Indian Journal of Pharmaceutical Science (2009), pp. 359-370.

X = Na

X = K

X = $NH_4^+$

FUNGICIDAL AGENT

CROSS-REFERENCE TO RELATED APPLICATIONS

This application is a U.S. National Stage of International Patent Application No. PCT/RU2014/000452, filed on Jun. 24, 2014, which application is incorporated by reference herein in its entirety. The International Application published on Dec. 30, 2015 as WO 2015/199572.

TECHNICAL FIELD

The invention relates to fungicidal agents and can be used for treating diseases caused by fungi and prevention of spoilage of various materials and agricultural products by fungi.

BACKGROUND ART

A very serious problem in modern medicine, veterinary medicine and plant cultivation is treatment of fungal, bacterial and viral diseases, many of which respond to therapy very poorly. This is due to lack of efficiency of existing drugs and variability of bacteria, leading to the emergence of resistant forms (see Fidel P. L. Jr, Vazquez J. A., Sobel J. D. *Candida glabrata*: review of epidemiology, pathogenesis and clinical disease with comparison to *C. albicans* 1999, 1:80-96. White T. Antifungal drug resistance in *Candida albicans* ASM News 8:427-433.

The above is important for veterinary medicine and industry, because there is deterioration of products due to development and spread of microorganisms.

There is a number of drugs for treatment of fungal infections: nystatin, amphotericin B, fluconazole and terbinafine (RLS medications Encyclopedia—2009, RLS, 2009. Moscow, 928). Each of them has significant drawbacks. Fluconazole exhibits mainly fungistatic effect and practically does not possess fungicidal properties [Pharmaceutical microbiology. Ed. by W. B. Hugo and A. D. Rassel Blackwell Scientific Publications, Oxford, 1987, 511 p].

Fluconazole may also be used to prevent deterioration of plants and agricultural products by fungi. It is also known that fluconazole is used in archive-keeping for paper treatment.

The main drawback of Nystatin is the low activity against multicellular fungi.

Amphotericin B is an active antifungal preparation, but it is very toxic.

There is a fungicidal agent, which is notable for the fact that it is a salt of 2,4-dioxo-5-(2-hydroxy-3,5-dichlorobenzylidene)amino-1,3-pyrimidine:

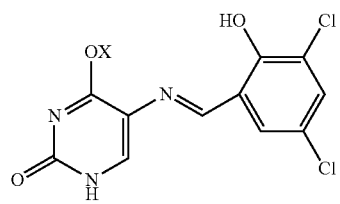

or its dimer:

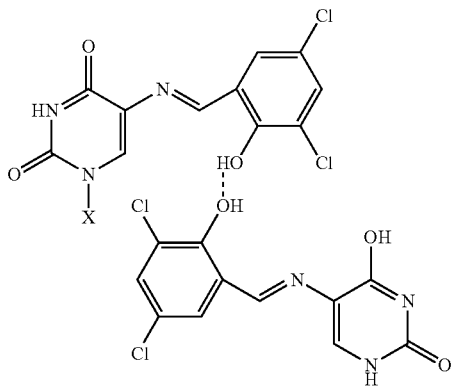

wherein X is selected from the series: $Na^+$, $K^+$, $Li^+$, $NH_4^+$, RU 2448960 Cl.

This technical solution is taken as a prototype of the present invention.

The drug has a pronounced antifungal activity with wide spectrum of effect.

However, this compound is very poorly soluble in aqueous media and in fats. The maximum value of solubility of the known drug in water is 0.002%, and for fats it is no more than 0.001% (octanol, which is a common model of lipids). The low solubility of the fungicidal agent prototype is due to the fact that the substance has a large particle size: length—30 mkm and section—about 300 nm, which does not promote dissolution of the substance neither in an aqueous medium nor in fats. Solutions with such concentration of the active substance are not sufficiently effective. At the same time the task of improvement of efficiency of use of a fungicidal agent in the form of solutions for use in human and veterinary medicine in the form of injections and inhalations and for treatment of a variety of materials and agricultural products is extremely urgent.

SUMMARY OF THE INVENTION

It is an object of the present invention to provide a fungicidal agent with wide spectrum of effect that is a highly soluble, which increases the efficiency of its use in the form of solutions.

According to the invention, the task set is solved by the synthesis of a fungicidal agent which is a salt associate 5-[3,5-rhothane-2-hydroxybenzylidene)amino]-4-hydrox-1H-pyrimidine-2-on with 1,2,3,4,5-pentahydroxy-6-methylaminohexane.

$CH_3NHCH_2CH(OH)CH(OH)CH(OH)CH(OH)CH_2OH$ (Б)

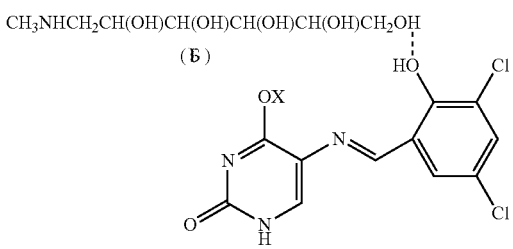

where X = Na, K, $NH_4^+$ (I)

The applicant has not found any technical solutions identical to the present invention, which enables to conclude that the invention conforms to the criterion "Novelty" (N).

All the salts specified in formula (I) have been isolated in crystalline form. FIG. 1-3 shows their photomicrographs.

To prove the associates' structure in formula (I), their proton magnetic resonance spectra in dimethylsulfoxide were recorded. A significant shift of the azomethine proton signal downfield (from 9.5 to 10 ppm) was registered, indicating the formation of a strong hydrogen bond.

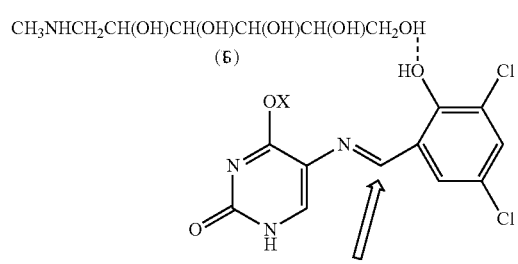

(A)

Length of 70% of the particles of the presented substance is less than 10 um, which provides an important new property of the object (technical effect): Increase in solubility in water up to concentrations of 0.3-0.4%, and for oil solutions—up to 0.25-0.3% (more than a hundred-fold magnification), which can significantly increase the efficiency of use of the drug solutions.

In the applicant's opinion, these circumstances enable to conclude that the presented technical solution conforms to the criterion "Inventive Step" ("IS").

PREFERRED EMBODIMENT

Figure 1:
FIG. 1-3 shows photomicrographs of the salts indicated in formula (I).
Figure 2:
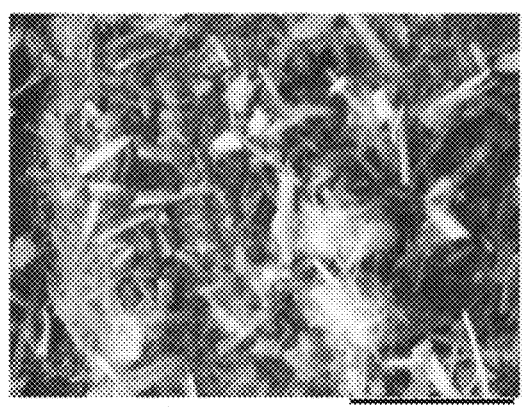
Figure 3:
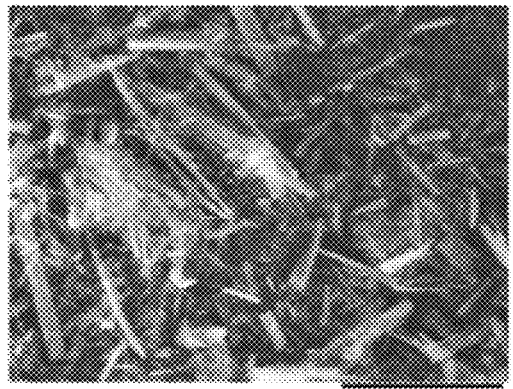

A 0.1% solution of the presented agent was prepared as follows.

0.04 g of sodium hydroxide and 10 ml of 96% ethanol were placed into a flask. The mixture was heated until complete dissolution of sodium hydroxide. 0.127 g of 5-aminouracil was added portionwise to the resulting solution at 40° C. Then, the resulting mass was heated in a boiling water bath up to complete dissolution of aminouracil. Also, 0.191 g of 3,5-dichlorosalicyl aldehyde was dissolved in 40 ml of 96% ethanol. The resulting solution was dropwise added to a stirred solution of 5-aminouracil sodium salt. After the formation of an orange-red precipitate, the reaction mixture heating was continued for 1.5 hours; after cooling of the reaction mass to room temperature the precipitate was filtered off, washed with 10 ml of 96% ethanol and dried. The resulting precipitate was transferred to a flask containing a prepared solution of 0.195 1,2,3,4,5-pentahydroxy-6-methylaminohexane in 300 ml of water. The reaction mixture was stirred at t=40° C. until complete dissolution of the precipitate. The resulting solution was cooled to room temperature.

Preparation of a higher concentration solutions of the presented substance is similar.

For treatment of fungi in medical, veterinary and agricultural purposes aqueous or oil solutions of the preparation at a concentration of 0.1% were used.

To prevent deterioration of various materials by fungi, aqueous solutions at a concentration of 0.3% were used.

Except for water, suitable solvents and transporters include isotonic sodium chloride solution, Ringer's solution and the like, wherein for a stabilizer can be used benzyl alcohol or any material suitable for this purpose; to increase the bioavailability, fluorocarbons can be used for suction activator. To prepare an oil solution of the drug is necessary to use non-volatile oils that are commonly used to produce oily solutions or suspensions.

Any non-volatile neutral oil, including synthetic mono- or diglycerides, and fatty acids, is suitable for this purpose. To make injectable preparations, oleic acid and glycerides, olive or castor oil (especially in their polyoxyethylated derivatives) can be used. The composition of oil solutions or suspensions may also contain stabilizers and detergents in the form of long chain alcohols or other similar substances. If the drug formulation is prepared in the form of an aqueous suspension for inhalation or nasal sprays, emulsifiers and substances conferring to the drug a sweet taste, a pleasant odor and color can be added to the active agent.

EXAMPLE 1

Treatment of Respiratory Diseases

The tests were conducted on white scrub mice (female, 6-8 weeks) received from "Rappolovo" breeding nursery (Leningrad reg.), which were kept under supervision for two weeks prior to the experiments on a standard diet in regulated vivarium conditions. Selection of the animals for the experiment group was conducted by the random selection method.

For propagation of *aspergillus* pneumonia, the white scrub mice received a single intraperitoneal injection of a cyclophosphamide solution (150 mg/kg). After 3 days, the mice received a single intraperitoneal injection of a hydrocortisone solution (250 mg/kg). Twenty-four hours after administration of hydrocortisone the mice were intranasally infected with a suspension of *Aspergillus niger* (approximately $10^7$ cells/ml) under ether narcosis.

On day 5 after infection 5 animals from each group were taken to study lung colonization (euthanasia in the rodents was performed by overdose of ether). Lung tissues were used to prepare homogenates, in which the titer of *Aspergillus* fungi was determined. Observation over the remaining mice was carried out for 14 days after infection to record their mortality.

The following groups of animals infected with *Aspergillus niger* were formed in the experiment.

1. Control groups: K1, K2, K3; the animals were exposed to an aerosol of isotonic sodium chloride solution.

2. Groups E1, E2, E3; the animals were administered a 0.1% aqueous solution of the presented preparation in the form of inhalations.

3. Groups P1, P2; the animals were administered an aqueous solution of the prototype fungicidal agent in the form of inhalations in concentrations of 0.002% and 0.001% respectively.

The animals were placed into an aerosol chamber (12 liters) for 30 minutes, during which period 500 mL of air pass through their lungs.

"OMRON U1" (Japan) ultrasonic nebulizer was used was used as an aerosol generator. To maintain a constant aerosol concentration in the chamber, a pneumatic vortex generator was used in the pulsed spraying mode ensuring a stable aerosol with particle size of 3 microns. The animals were placed in immobilization containers and exposed to the obtained aerosol for 30 minutes 1 time per day for 3 days starting from day 1 after the infection.

Samples of homogenized lung tissue were used to prepare a number of successive dilutions followed by sowing on Saburo medium. The results obtained are shown in Table 1.

The results shown in Table 1 confirm the effective antifungal activity of the presented fungicidal agent.

Results of the study of the fungicidal agent's antifungal effect

TABLE 1

| Groups of animals | Number of colonies (in different dilutions) | | |
|---|---|---|---|
| | $10^{-2}$ | $10^{-4}$ | $10^{-6}$ |
| K1 | 75 | 2 | — |
| K2 | 64 | 2 | — |
| K3 | 48 | — | — |
| E1 | 4 | — | — |
| E2 | 4 | — | — |
| E3 | 2 | — | — |
| П1 | 26 | 1 | — |
| П2 | 37 | 2 | — |

EXAMPLE 2

Treatment of a Fungal Disease of the Skin—Scaly Skin Disease (Tinea Versicolor, Pityriasis Versicolor)

The disease is caused by a fungus called *Pityrosporum orbiculare—Malassezia furfur* (mycelial form).

The following was prepared for the study: A 0.1% oil (olive oil) solution of the presented preparation and a 0.002% aqueous solution of the prototype substance. As a reference olive oil was used. The study included three groups of patients. Each group included 2 patients with this pathology. Treatment duration was 7 days. The drug was applied with a cotton swab 2 times a day—in the morning and in the evening.

As a criterion for mycological cure was considered the absence of yeast and mycelial forms of the *Malassezia* fungi, and the criterion of complete cure was the absence of clinical symptoms and fungi of the *Malassezia* genus in skin scales obtained from the skin at the areas of disappeared lesions.

The results of the study are shown in Table 2.

Results of Treatment of a Fungal Disease of the Skin—Scaly Skin Disease (Tinea Versicolor, Pityriasis Versicolor)

TABLE 2

| Preparation | Mycological cure | Complete cure |
|---|---|---|
| 1 Reference | 2 Absent | 3 Absent |
| 1 The presented preparation | 2 yeast and mycelial forms of the *Malassezia* genus fungi are absent | 3 Reached |
| Prototype | A slight decrease in yeast and mycelial forms of the *Malassezia* genus fungi | Absent |

Thus, a pronounced positive effect was achieved only when using the presented preparation.

EXAMPLE 3

Treatment of Vulvovaginal Candidiasis

In the experiment, the patients, who suffered vulvovaginal candidiasis caused by *Candida* fungi, were treated using the following aqueous solutions: 1) 0.1% solution of the presented drug (3 persons), 2) 0.002% solution of the prototype drug (3 people).

The treatment in the form of dualfold (in the morning and in the evening) douchings was performed for 7 days. The treatment efficacy was assessed by the clinical presentation and the results mycological examination (inoculations on Saburo medium). The results of the study are shown in Table 3.

Results of Treatment of Vulvovaginal Candidiasis

TABLE 3

| Preparation | Mycological cure | Complete cure |
|---|---|---|
| Presented | A tenfold reduction in the number of fungi inoculated on a solid medium. | Reached |
| Prototype | 1.7-fold reduction in the number of fungi inoculated on a solid medium. | Not reached |

Thus, the use of the presented preparation allows to achieve a complete cure of *Candida* infection, whereas patients treated with an aqueous solution of the prototype substance showed a slight decrease of contamination by the fungus while maintaining the main complaints and manifestations of the infection.

EXAMPLE 4

Treatment of Fungal Diseases in Plants

The study was conducted on tuberous begonias (*Begonia tuberosa hybridum*), infected with powdery mildew. Powdery mildew affects many plants, including trees and shrubs. Powdery mildew affects chrysanthemums, begonias, roses; at that a white, sometimes darkening, plaque appears green parts of the plant. The disease is transmitted by airborne spores.

The tested plants were infected with spores of a fungus (*Leveillula taurica*) when exposed up to appearance of a white plaque on the leaves. Three leaves on each plant were infected. After appearance of the plaque the plants in control group (three plants) were isolated from the three plants treated with a spray of a 0.1% aqueous solution of the presented preparation. The treatment was performed once a day for 7 days. After the treatment was complete, observation over the plants was continued for another three weeks. During the observation the control group plants showed an increase in the amount of plaque, which was a fungal mycelium, and the number of leaves infected increased on average up to 5-7, with plaque covering stems as well. The plants treated with the tested substance, no increase or spread of the fungus to other parts of the plant occur. When flushed off the leaf and inoculated on a nutrient medium, no growth of the fungi was observed.

EXAMPLE 5

Treatment of Fungal Diseases in Animals

The preparation was used in treatment of ringworm in cats (two animals) caused by fungi of the *Microsporum* genus and characterized by appearance of small round bald patches on the face and ears of the animal. The preparation in the form of a 0.1% aqueous solution was applied onto the affected area three times a day for 6 days.

As a result of the treatment, the affected areas ceased to increase, disappearance of inflammatory manifestations was reported. Inoculations of the swabs from the affected area after the treatment did not lead to growth on nutrient media.

Thus, use of the presented formulation was effective for treatment of dermatomycosis caused by *Microsporum* fungus.

EXAMPLE 6

Protection of Construction Wood Against Fungal Attacks

To test the preparation boards by the dimensions of 20×40×2 cm were used. The boards were divided into three groups. Group 1: the boards were impregnated with a 0.3% aqueous solution of the presented formulation. The impregnation was carried out by twofold application of the solution by means of a diffuser with an intermediate drying. Group 2: the boards were impregnated with a 0.02% aqueous solution of the prototype preparation. The impregnation was carried out by twofold application of the solution by means of a diffuser with an intermediate drying. Group 3 (control): the boards were impregnated with distilled water. The impregnation was carried out by twofold application of water by means of a diffuser with an intermediate drying.

The boards dried after treatment were soaked in water for two hours, after which they were coated with *Aspergillus niger* and *Penicillium notatum* fungi cultures at opposite ends of one side. The boards were placed in thermostats for 5 days at the temperature of 30° C. in a humid environment. After incubation, the boards were visually inspected and inoculations were made from their surface onto a nutrient medium (Sabouraud).

The result revealed that on the boards in the control group or those treated with a 0.02% aqueous solution of the prototype preparation a growth of the inoculated test bacteria can be detected, which later spread in the nutrient medium. No growth of the test organisms was registered on the boards impregnated with a 0.3% solution of the presented fungicidal agent, and the control inoculations did not lead to a growth on the nutrient medium.

INDUSTRIAL APPLICABILITY

The invention is implemented using common materials and equipment, resulting, according to the applicant's opinion, in compliance of the invention with the "Industrial Applicability" ("IA") patentability criterion.

The invention claimed is:
1. A compound of formula

CH$_3$NHCH$_2$CH(OH)CH(OH)CH(OH)CH(OH)CH$_2$OH

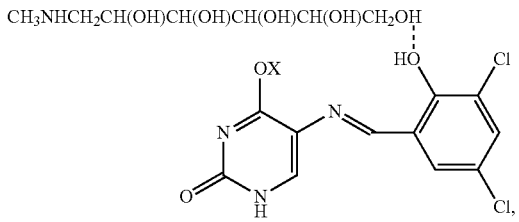

wherein X is selected from the group consisting of: Na$^+$, K$^+$ and NH$_4^+$; and a dotted line is a hydrogen bond.

2. The compound of claim 1, wherein X is Na$^+$.
3. The compound of claim 1, wherein X is K$^+$.
4. The compound of claim 1, wherein X is NH$_4^+$.
5. A composition comprising the compound of claim 1 and a carrier and/or excipient.
6. The composition of claim 5 wherein the composition comprises from about 0.001% to about 0.4% of the compound.
7. The composition of claim 5, wherein the carrier is selected from the group consisting of water, a sodium chloride solution, and Ringer's solution.
8. The composition of claim 5, wherein the carrier is an oil.
9. The composition of claim 8, wherein the oil is selected from the group consisting of monoglycerides, diglycerides, fatty acids, olive oil, castor oil, and polyoxyethylated oil derivatives.
10. The composition of claim 5, wherein the excipient is selected from the group consisting of a stabilizer, a detergent, an emulsifier, a suction activator, a sweetener, an aromatizer, a colorant, and any combinations thereof.
11. The composition of claim 10, wherein the stabilizer is benzyl alcohol.
12. The composition of claim 10, wherein the detergent is a long-chain alcohol.
13. The composition of claim 10, wherein the suction activator is a fluorocarbon.
14. The compound of claim 1, wherein the compound is prepared by the process:
providing a solution comprising XOH and ethanol at a temperature of at least about 40° C.;
adding 5-aminouracil to said solution to afford a reaction mixture;
heating said reaction mixture to a temperature of at least about 100° C.;
adding a solution of 3.5-dichlorosalicyl aldehyde in ethanol to said heated reaction mixture to form a precipitate;
isolating the precipitate;
adding the precipitate to an aqueous solution of 1,2,3,4,5-pentahydroxy-6-methylaminohexane, and isolating the resulting compound.
15. A method for preparing the compound of claim 1 comprising:
providing a solution comprising XOH and ethanol at a temperature of at least about 40° C.;
adding 5-aminouracil to said solution to afford a reaction mixture;
heating said reaction mixture to a temperature of at least about 100° C.;
adding a solution of 3.5-dichlorosalicyl aldehyde in ethanol to said heated reaction mixture to form a precipitate;
isolating the precipitate;
adding the precipitate to an aqueous solution of 1,2,3,4,5-pentahydroxy-6-methylaminohexane, and isolating the resulting compound.
16. A pharmaceutical dosage form comprising the compound of claim 1 and a pharmaceutically acceptable carrier and/or excipient.
17. The pharmaceutical dosage form of claim 16, wherein the dosage form is suitable for topical administration.
18. The pharmaceutical dosage form of claim 16, wherein the dosage form is suitable for mucosal administration.
19. The pharmaceutical dosage form of claim 16, wherein the dosage form is suitable for intranasal administration or administration by inhalation.
20. The pharmaceutical dosage form of claim 16, wherein the dosage form is suitable for intravaginal administration.

21. The pharmaceutical dosage form of claim 16, wherein the dosage form is in the form of a spray.

22. The pharmaceutical dosage form of claim 16, wherein the dosage form is in the form of a solution or a suspension.

23. A method for preventing or inhibiting growth of a fungus comprising administering an effective amount of the compound of claim 1.

24. The method of claim 23 wherein the fungus is from a taxa selected from the group consisting of *Candida, Aspergillus, Penicillium, Microsporum, Pityrosporum, Malassezia*, and *Leveillula*.

25. A method for preventing or inhibiting growth of a fungus comprising administering an effective amount of the composition of claim 5.

26. A method for treating a fungal infection in a subject in need thereof comprising administering to the subject an effective amount of the compound of claim 1.

27. The method of claim 26, wherein the fungal infection is selected from a respiratory infection, a skin infection, and a vaginal infection.

28. The method of claim 26, wherein the fungal infection is a mucosal infection.

29. The method of claim 26, wherein the fungal infection is selected from the group consisting of fungal pneumonia, tinea versicolor, pityriasis versicolor, dermatomycosis, vulvovaginal candidiasis, ringworm, and powdery mildew.

30. The method of claim 26, wherein the treatment is conducted for at least 7 days.

31. A method for treating a fungal infection in a subject in need thereof comprising administering to the subject an effective amount of the composition of claim 5.

32. A method for treating a fungal infection in a subject in need thereof comprising administering to the subject the pharmaceutical dosage form of claim 16.

\* \* \* \* \*